United States Patent [19]

Smith

[11] 4,167,581

[45] Sep. 11, 1979

[54] ALKANOLAMINE DERIVATIVES AND PHARMACEUTICAL COMPOSITIONS AND USES THEREOF

[75] Inventor: Leslie H. Smith, Macclesfield, England

[73] Assignee: Imperial Chemical Industries Limited, London, England

[21] Appl. No.: 956,986

[22] Filed: Nov. 1, 1978

Related U.S. Application Data

[60] Continuation-in-part of Ser. No. 880,495, Feb. 23, 1978, Pat. No. 4,131,685, which is a division of Ser. No. 738,173, Nov. 2, 1976, Pat. No. 4,083,992, which is a division of Ser. No. 607,995, Aug. 26, 1975, Pat. No. 4,010,189, which is a division of Ser. No. 421,669, Dec. 4, 1973, Pat. No. 3,928,412.

[30] Foreign Application Priority Data

Dec. 15, 1972 [GB] United Kingdom .............. 57970/72

[51] Int. Cl.$^2$ ................. A61K 31/275; A61K 31/165; C07C 121/50; C07C 121/60
[52] U.S. Cl. .................................... 424/304; 424/324; 424/286; 424/300; 260/465 D
[58] Field of Search ............... 424/304, 324, 286, 300; 260/557 R, 558 AD, 558 P, 559, 465 D, 562 A, 562 B

[56] References Cited

U.S. PATENT DOCUMENTS

| | | | |
|---|---|---|---|
| 3,459,782 | 8/1969 | Koppe et al. | 260/465 |
| 3,663,607 | 5/1972 | Barrett et al. | 260/465 X |
| 3,712,927 | 1/1973 | Howe et al. | 260/465 X |
| 3,732,277 | 5/1973 | Koppe et al. | 260/465 |
| 3,933,911 | 1/1976 | Main | 424/324 |
| 3,961,072 | 6/1976 | Cox et al. | 424/324 |
| 4,010,189 | 3/1977 | Smith | 260/465 D |
| 4,034,106 | 7/1977 | Smith | 424/324 |
| 4,041,075 | 8/1977 | Smith | 424/324 |

*Primary Examiner*—Albert T. Meyers
*Assistant Examiner*—D. W. Robinson
*Attorney, Agent, or Firm*—Cushman, Darby & Cushman

[57] ABSTRACT

1-Aryloxy-3-aminoalkylamino-2-propanol derivatives, processes for their manufacture, pharmaceutical compositions containing them and methods of using them in the treatment of heart diseases. The compounds possess β-adrenergic blocking activity and some of them additionally possess cardiac stimulant activity. Representative of the compounds disclosed is 1-(2-cyanophenoxy)-3-β(4-hydroxyphenylacetamido)ethylamino-2-propanol.

14 Claims, No Drawings

ALKANOLAMINE DERIVATIVES AND PHARMACEUTICAL COMPOSITIONS AND USES THEREOF

This application is a divisional continuation-in-part of application Ser. No. 880,495, filed Feb. 23, 1978 now U.S. Pat. No. 4,131,685 as a division of application Ser. No. 738,173, filed Nov. 2, 1976, now U.S. Pat. No. 4,083,992, which itself is a division of application Ser. No. 607,995, filed Aug. 26, 1975, now U.S. Pat. No. 4,010,189, which in turn is a division of application Ser. No. 421,669, filed Dec. 4, 1973, now U.S. Pat. No. 3,928,412.

This invention relates to new alkanolamine derivatives which possess β-adrenergic blocking activity and which are selected from compounds of the formula:

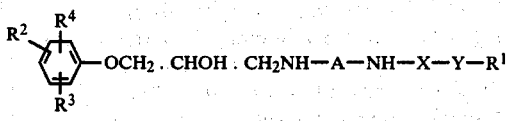

wherein A is alkylene of from 2 to 12 carbon atoms, wherein $R^1$ is hydrogen, or alkyl, halogenoalkyl, alkenyl or cycloalkyl each of up to 10 carbon atoms, or aryl of the formula:

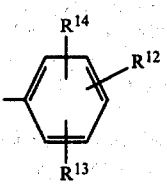

wherein $R^2$, $R^3$, $R^{12}$ and $R^{13}$, which may be the same or different, each is hydrogen, halogen, hydroxy, amino, nitro or cyano, alkyl, cycloalkyl, alkenyl, alkynyl, alkoxy, alkylthio, cycloalkoxy, alkenyloxy, alkynyloxy or alkanoyl each of up to 6 carbon atoms, or aryl, aryloxy or aralkoxy each of up to 12 carbon atoms; or wherein $R^2$ and $R^3$ together, and/or $R^{12}$ and $R^{13}$ together, are trimethylene, tetramethylene, 1-oxo-tetramethylene, propenylene, but-2-enylene or buta-1,3-dienylene such that together with the adjacent benzene ring they form respectively indanyl, 5,6,7,8-tetrahydronaphthyl, 5-oxo-5,6,7,8-tetrahydronaphthyl, indenyl, 5,8-dihydronaphthyl or naphthyl; wherein $R^4$ is hydrogen, hydroxy or hydroxymethyl or aralkoxy of up to 12 carbon atoms; wherein $R^{14}$ is hydrogen, amino or dialkylamino of up to 12 carbon atoms; wherein X is carbonyl (—CO—) and wherein Y is a direct link, or alkylene, oxyalkylene or alkyleneoxy each of up to 6 carbon atoms, or (except when $R^1$ is hydrogen) is oxygen; and the acid-addition salts thereof.

It will be observed that the alkanolamine derivative of the invention possesses an asymmetric carbon atom, namely the carbon atom of the —CHOH— group in the alkanolamine side-chain, and it can therefore exist in racemic and optically-active forms. It is to be understood that this invention encompasses the racemic form of the alkanolamine derivative and any optically-active form which possesses β-adrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the "S" absolute configuration of the said —CHOH— group.

A suitable value for A is, for example, ethylene, trimethylene, tetramethylene, hexamethylene, dodecamethylene, 1-methylethylene, 2-methylethylene or 1,1-dimethylethylene. A is preferably ethylene, 1-methylethylene or 1,1-dimethylethylene.

A suitable value for $R^1$ when it is alkyl, halogenoalkyl, alkenyl or cycloalkyl is, for example, methyl, ethyl, n-propyl, isopropyl, n-butyl, isobutyl, t-butyl, n-pentyl, n-octyl, trifluoromethyl, allyl, cyclopropyl, cyclopentyl or cyclohexyl.

A suitable value for $R^2$, $R^3$, $R^{12}$ or $R^{13}$ when it is halogen is, for example, fluorine, chlorine, bromine or iodine.

A suitable value for $R^2$, $R^3$, $R^{12}$ or $R^{13}$ when it is alkyl, cycloalkyl, alkenyl, alkynyl, alkoxy, alkylthio, cycloalkoxy, alkenyloxy, alkynyloxy or alkanoyl is, for example, methyl, ethyl, n-propyl, cyclopropyl, cyclopentyl, allyl, ethynyl, methoxy, isopropoxy, methylthio, cyclopentyloxy, allyloxy, propargyloxy, formyl or acetyl.

A suitable value for $R^2$, $R^3$, $R^{12}$ or $R^{13}$ when it is aryl or aryloxy is, for example, phenyl or phenoxy.

A suitable value for $R^2$, $R^3$, $R^4$, $R^{12}$ or $R^{13}$ when it is aralkoxy is, for example, benzyloxy.

A suitable value for $R^{14}$ when it is dialkylamino is, for example, dimethylamino.

A suitable value for Y when it is alkylene, oxyalkylene or alkyleneoxy is, for example, methylene, ethylene, oxymethylene, methyleneoxy, ethyleneoxy, trimethyleneoxy, 1-methylethylideneoxy or 1-methylpropylideneoxy.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

A preferred alkanolamine derivative of the invention is a compound of the formula given above wherein A is ethylene, 1-methylethylene or 1,1-dimethylethylene and wherein either (a) $R^1$ is hydrogen, or alkyl, alkenyl or cycloalkyl each of up to 6 carbon atoms, or trifluoromethyl or monohydroxyphenyl or dihydroxyphenyl, Y is a direct link, X is carbonyl, $R^2$ is hydrogen, chloro, cyano, nitro, methyl, allyl, methoxy or allyloxy in the ortho-position of the benzene ring and $R^3$ and $R^4$ are both hydrogen; or (b) $R^1$ is phenyl, $R^{12}$ is hydrogen, chloro, nitro, hydroxy, methyl or methoxy, $R^{13}$ and $R^{14}$ are both hydrogen, Y is methylene, ethylene or methyleneoxy. X is carbonyl, $R^2$ is hydrogen or chloro, cyano, nitro, methyl, allyl, methoxy or allyloxy in the ortho- or meta-position of the benzene ring and $R^3$ and $R^4$ are both hydrogen; or (c) $R^1$ is hydrogen or alkyl of up to 6 carbon atoms, Y is methyleneoxy, X is carbonyl and $R^2$, $R^3$ and $R^4$ have the meanings stated in paragraph (a) above; or (d) $R^1$ is alkyl or cycloalkyl each of up to 6 carbon atoms, or phenyl, $R^{12}$ is hydrogen, methyl, methoxy or phenyl, $R^{13}$ and $R^{14}$ are both hydrogen, Y is a direct link or methylene, X is carbonyl, $R^2$ is hydrogen or hydroxy, $R^3$ is hydrogen and $R^4$ is hydroxy; or (e) $R^1$ is alkyl of up to 6 carbon atoms, Y is oxygen or methyleneoxy, X is carbonyl and $R^2$, $R^3$ and $R^4$ have the meanings stated in paragraph (d) above;

or an acid-addition salt thereof.

Specific alkanolamine derivatives of the invention are those hereinafter described in the Examples. Of these, preferred compounds by virtue of their high cardioselective β-adrenergic blocking activity (as hereinafter defined) are:

1-phenoxy-3-β-benzamidoethylamino-2-propanol;
1-phenoxy-3-β-phenylacetamidoethylamino-2-propanol;
1-phenoxy-3-β-phenoxyacetamidoethylamino-2-propanol;
1-phenoxy-3-(α-methyl-β-phenylacetamidoethyl-)amino-2-propanol;
1-phenoxy-3-β-pivalamidoethylamino-2-propanol;
1-phenoxy-3-(β-isobutyramido-α-methylethyl)amino-2-propanol;
1-(2-nitrophenoxy)-3-β-isobutyramidoethylamino-2-propanol;
1-phenoxy-3-β-propionamidoethylamino-2-propanol;
1-phenoxy-3-β-hydroxyacetamidoethylamino-2-propanol;
1-(2-cyanophenoxy)-3-β-propionamidoethylamino-2-propanol;
1-phenoxy-3-β-(2-chlorophenylacetamidoethyl)amino-2-propanol;
1-phenoxy-3-β-butyramidoethylamino-2-propanol;
1-phenoxy-3-β-isobutyramidoethylamino-2-propanol;
1-phenoxy-3-β-(4-methoxyphenylacetamidoethyl-)amino-2-propanol;
1-phenoxy-3-β-acetamidoethylamino-2-propanol;
1-(2-methoxyphenoxy)-3-β-isobutyramidoethylamino-2-propanol;
1-phenoxy-3-(α,α-dimethyl-β-isobutyramidoethyl)-amino-2-propanol;
1-phenoxy-3-(α,α-dimethyl-β-phenylacetamidoethyl)-amino-2-propanol; and
1-(2-cyanophenoxy)-3-β-(4-hydroxyphenylacetamido)-ethylamino-2-propanol;
and the acid-addition salts thereof.

Preferred compounds by virtue of their high level of cardiac stimulant activity (as hereinafter defined) are:
1-(3,4-dihydroxyphenoxy)-3-β-isobutyramidoethylamino-2-propanol and the acid-addition salts thereof.

The alkanolamine derivative of the invention may be manufactured by any chemical process known to be useful for the manufacture of chemically-analogous compounds, particularly these processes disclosed in U.S. Pat. No. 4,010,189.

A preferred process for the manufacture of the alkanolamine derivative of the invention comprises the reaction of a compound of the formula:

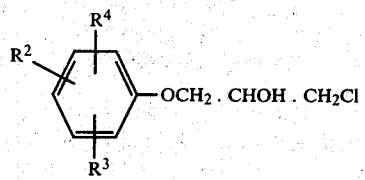

or

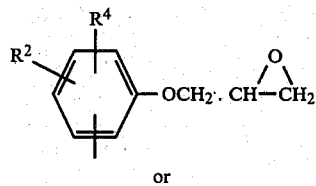

-continued

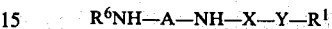

wherein $R^2$, $R^3$ and $R^4$ have the meanings stated above (both of which compounds may be obtained by the reaction of the corresponding phenol with epichlorohydrin), with an amine of the formula:

$$R^6NH-A-NH-X-Y-R^1$$

wherein A, $R^1$, X and Y have the meanings stated above and wherein $R^6$ is hydrogen or benzyl, whereafter if $R^6$ is benzyl this is removed by hydrogenolysis.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses β-adrenergic blocking activity, and furthermore this activity is cardio-selective. This activity may be determined by the reversal of isoprenaline-induced tachycardia in rats or cats, a standard test for the determination of β-adrenergic blocking activity, and by relative freedom from antagonism of isoprenaline-induced vasodilation in cats or of the relief produced by isoprenaline of histamine-induced bronchospasm in guinea-pigs. Compounds exhibiting this cardioselective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathominetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is three to ten times more active as a cardioselective β-adrenergic blocking agent than practolol. At doses of an alkanolamine derivative of the invention which produce effective β-adrenergic blockade in rats or cats, no symptoms of toxicity are apparent.

Some of the alkanolamine derivatives of the invention wherein one or more of the substituents $R^2$, $R^3$ and $R^4$ stands for the hydroxy radical, and in particular those wherein $R^4$ stands for a hydroxy radical in the 3- or 4-position of the benzene nucleus, $R^2$ stands for the hydrogen atom or for a hydroxy radical in the 3-position when $R^4$ is in the 4-position of the benzene nucleus and $R^3$ stands for the hydrogen atom possess, in addition to β-adrenergic blocking activity, substantial cardiac stimulant activity. This may be demonstated in either conscious or pentobarbitone-anaesthetised dogs, where the alkanolamine derivative or salt thereof produces an increase in heart rate, and/or an increase in force of contraction of the heart, and an increase in the speed of conduction of electrical activity through the tissues of the heart. Unlike isoprenaline, a known cardiac stimulating agent, a preferred stimulant alkanolamine derivative of the invention or a salt thereof is well absorbed when administered orally and has a substantial duration of action. At doses of an alkanolamine derivative of the invention which produce effective cardiac stimulation in dogs, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; α-adrenergic blocking agents, for example phentolamine and sympathomimetic bronchro-dilators, for example isoprenaline, orciprenaline, adrenaline and ephedrine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

When used for the treatment of acute or chronic heart failure in man, it is expected that a cardiac stimulant alkanolamine derivative would be given to man at a total oral dose of between 10 mg. and 200 mg. daily, at doses spaced at 6–8 hourly intervals, or at an intravenous dose of between 1 mg. and 100 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1%w/v of active ingredient, and more particularly containing 0.1%w/v of active ingredient.

The invention is illustrated but not limited by the following Examples:

EXAMPLE 1

A mixture of 3.0 g. of 2,3-epoxy-1-phenoxypropane, 50 ml. of n-propanol, 4.0 g. of β-benzamidoethylamine hydrochloride and a solution of 0.8 g. of sodium hydroxide in 5 ml. of water is heated under reflux for 18 hours. The mixture is evaporated to dryness under reduced pressure and the residue is stirred with 40 ml. of aqueous 2 N-hydrochloric acid. The mixture is filtered and the solid residue is crystallised from ethanol. There is thus obtained 3-β-benzamidoethylamino-1-phenoxy-2-propanol hydrochloride, m.p. 198°–199° C.

The process described above is repeated except that the appropriate 2,3-epoxy-1-phenoxypropane (or the corresponding 3-chloro-1-phenoxy-2-propanol) and the appropriate β-carboxamidoethylamine are used as starting materials. There are thus obtained the compounds described in the following table:

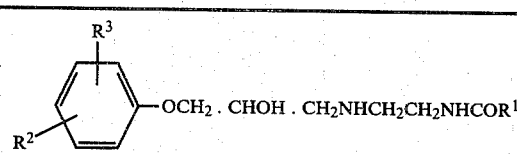

—OCH$_2$ . CHOH . CH$_2$NHCH$_2$CH$_2$NHCOR$^1$

| R$^1$ | R$^2$ | R$^3$ | m.p.(°C.) | Crystallisation solvent |
|---|---|---|---|---|
| methyl | H | H | 103–105 | ethyl acetate |
| ethyl | H | H | 126–127 | acetonitrile |
| n-propyl | H | H | 86–87 | ethyl acetate |
| isopropyl | H | H | 125–126 | ethyl acetate |
| n-octyl | H | H | 95–96 | ethyl acetate |
| cyclopropyl | H | H | 125–126 | ethyl acetate |
| cyclopentyl | H | H | 133–135 | ethyl acetate |
| cyclohexyl | H | H | 138–139 | acetonitrile |
| 2-chlorophenyl | H | H | hydrochloride 182–183 | acetonitrile |
| 4-tolyl | H | H | hydrochloride | acetonitrile |

-continued $R^3$-phenyl-OCH$_2$.CHOH.CH$_2$NHCH$_2$CH$_2$NHCOR$^1$ with $R^2$ substituent

| R$^1$ | R$^2$ | R$^3$ | m.p.(°C.) | Crystallisation solvent |
|---|---|---|---|---|
| 2-nitrophenyl | H | H | 211–212 131–132 | ethyl acetate/ petroluem ether |
| 2-methoxyphenyl | H | H | hydrogen oxalate 164–165 | ethanol |
| 2-dimethyl- aminophenyl | H | H | 82–84 | ethyl acetate |
| isopropyl | 2-cyano | H | 109–110 | ethyl acetate |
| isopropyl | 2-nitro | H | 108–110 | ethyl acetate |
| isobutyl | H | H | 114–115 | ethyl acetate |
| t-butyl | H | H | hydrogen oxalate 167–168 | ethanol |
| n-pentyl | H | H | 101–102 | ethyl acetate |
| ethyl | 2-cyano | H | 96–97 | ethyl acetate/ petroleum ether |
| isopropyl | 2-chloro | H | 129–130 | ethyl acetate |
| isopropyl | 2-methyl | H | 120–122 | ethyl acetate |
| isopropyl | 2-methoxy | H | 142–143 | acetonitrile |
| isopropyl | 2-chloro | 4-methyl | 119–120 | ethyl acetate |
| isopropyl | 2-chloro | 5-chloro | 152–153 | acetonitrile |
| isopropyl | 2-nitro | 4-methoxy | 122–124 | ethyl acetate |
| methyl | 3-cyano | H | 121–122 | ethyl acetate |
| 4-benzyloxy- phenyl | H | H | 124–126 | acetonitrile |
| isopropyl | 2-benzyloxy | H | 137–138 | acetonitrile |
| 3,4-dibenzyloxy- phenyl | H | H | hydrochloride 223–224 | ethanol |
| t-butyl | 2-cyano | H | 152–154 | acetonitrile |
| t-butyl | 2-nitro | H | 165–166 | acetonitrile |
| isopropyl | 2-allyl | H | 112–113 | ethyl acetate/ cyclohexane |
| isopropyl | 2-allyloxy | H | 119–120 | ethyl acetate |
| 4-cyanophenyl | 2-chloro | H | hydrochloride 167–169 | ethyl acetate |
| methyl | 2-chloro | H | 83–85 | ethylacetate |
| methyl | 2-methyl | H | 93–95 | ethyl acetate |
| methyl | (1-naphthyl) | | 136–138 | ethyl acetate/ isopropanol |
| n-propyl | 2-cyano | H | 102–104 | ethyl acetate |
| isopropyl | (1-naphthyl) | | 125–127 | ethyl acetate |
| n-butyl | 2-cyano | H | 125–127 | ethyl acetate |
| t-butyl | 2-chloro | H | oxalate 187–188 | aqueous ethanol |
| n-pentyl | 2-cyano | H | 100–102 | ethyl acetate |

EXAMPLE 2

A mixture of 1.5 g. of 2,3-epoxy-1-phenoxypropane, 50 ml. of n-propanol, 2.31 g. of β-phenoxyacetamidoethylamine hydrochloride and a solution of 0.4 g. of sodium hydroxide in 5 ml. of water is heated under reflux for 18 hours. The mixture is evaporated to dryness under reduced pressure and the residue is stirred with 20 ml. of aqueous N-sodium hydroxide solution. The mixture is extracted three times with 20 ml. of ethyl acetate each time, and the combined extracts are dried over anhydrous magnesium sulphate and filtered. The filtrate is added to a solution of 2.5 g. of oxalic acid in 100 ml. of ether. The mixture is filtered and the solid residue is crystallised from acetonitrile. There is thus obtained 1-phenoxy-3-β-phenoxyacetamidoethylamino-2-propanol oxalate, m.p. 131°–133° C.

EXAMPLE 3

A mixture of 1.5 g. of 2,3-epoxy-1-phenoxypropane, 50 ml. of n-propanol, 2.15 g. of β-phenylacetamidoethylamine hydrochloride and a solution of 0.4 g. of sodium hydroxide in 5 ml. of water is heated under reflux for 18 hours. The mixture is evaporated to dryness under reduced pressure and the residue is stirred with 20 ml. of aqueous N-sodium hydroxide solution. The mixture is extracted three times with 20 ml. of ethyl acetate each time and the combined extracts are dried over anhydrous magnesium sulphate and filtered. The filtrate is evaporated to dryness under reduced pressure and the residue is crystallised from ethyl acetate. There is thus obtained 1-phenoxy-3-β-phenylacetamidoethylamino-2-propanol, m.p. 124°–125° C.

The process described above is repeated except that the appropriate 2,3-epoxy-1-phenoxypropane and the appropriate β-carboxamidoethylamine are used as starting materials.

There are thus obtained the compounds described in the following table:

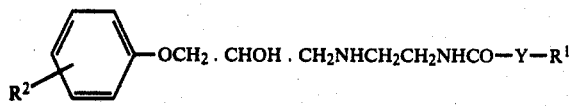

$R^2$-C6H4-OCH2.CHOH.CH2NHCH2CH2NHCO—Y—R¹

| R¹ | Y | R² | m.p. (°C.) | Crystallisation solvent |
|---|---|---|---|---|
| 4-chlorophenyl | —CH₂— | H | 119–120 | acetonitrile |
| 2-chlorophenyl | —CH₂— | H | 137–138 | ethyl acetate |
| phenyl | —CH₂CH₂— | H | 112–113 | ethyl acetate/petroleum ether |
| 4-chlorophenyl | —CH₂O— | H | 163–164 | methanol |
| phenyl | —CH₂CH₂CH₂O— | H | 89–91 | ethyl acetate/petroleum ether |
| ethyl | —O— | H | 87–88 | ethyl acetate/petroleum ether |
| H | —CH₂O— | H | hydrogen oxalate 128–129 | ethanol |
| methyl | —CH₂O— | H | hydrogen oxalate 135–137 (with decomposition) | ethanol |
| 2-nitrophenyl | —CH₂— | H | 130–131 | ethyl acetate |
| 4-nitrophenyl | —CH₂— | H | 135–136 | ethyl acetate |
| 4-methoxyphenyl | —CH₂— | H | 122–123 | ethyl acetate |
| 2-chlorophenyl | —CH₂— | 2-cyano | 120–122 | acetonitrile |
| 2-chlorophenyl | —CH₂— | 2-chloro | 144–146 | ethyl acetate |
| 4-chlorophenyl | —C(CH₃)₂O— | H | hydrogen oxalate 172–174 | ethanol |
| 2-methoxyphenyl | —CH₂O— | H | hydrogen oxalate 156–158 | acetonitrile |
| phenyl | —CH₂— | 2-cyano | 142–143 | isopropanol |
| phenyl | —CH₂— | 2-chloro | 133–134 | isopropanol |
| phenyl | —CH₂— | 2-methyl | 126–127 | ethyl acetate |
| phenyl | —CH₂— | 3-methyl | 100–101 | ethyl acetate |
| phenyl | —CH₂— | 4-methyl | 123–124 | ethyl acetate |
| phenyl | —CH₂— | 2-methoxy | 117 | ethyl acetate |
| phenyl | —CH₂— | 2-nitro | 125–126 | ethyl acetate |
| phenyl | —CH₂O— | 2-cyano | oxalate 130–132 | acetonitrile |
| 2-chlorophenyl | —CH₂— | (1-naphthyl) | hydrochloride 176–177 | acetonitrile |
| 1-naphthyl | —CH₂— | (1-naphthyl) | 79–80 | ethyl acetate |
| ethyl | —O— | 2-chloro | oxalate 88–90 | acetonitrile |
| 4-hydroxyphenyl | —CH₂CH₂— | H | 88–89 (d) | ethanol |
| phenyl | —CH₂— | (1-naphthyl) | 114–117 | ethyl acetate |
| phenyl | —CH₂CH₂O— | (1-naphthyl) | hemioxalate dihydrate 166–168 | aqueous ethanol |

EXAMPLE 4

A mixture of 1.5 g. of 2,3-epoxy-1-phenoxypropane, 50 ml. of n-propanol and 1.92 g. of 1-methyl-2-(phenylacetamido)ethylamine is heated under reflux for 18 hours. The mixture is evaporated to dryness under reduced pressure and the residue is crystallised from ethyl acetate. There is thus obtained 1-phenoxy-3-(α-methyl-β-phenylacetamido ethyl)amino-2-propanol, m.p. 124°–126° C.

The process described above is repeated except that the appropriate 2,3-epoxy-1-phenoxypropane and the appropriate β-carboxamidoalkylamine are used as starting materials. There are thus obtained the compounds described in the following table:

$R^2$-C6H4-OCH2.CHOH.CH2NH—A—NHCO—Y—R¹

| R¹ | Y | A | R² | m.p.(°C.) | Crystallisation solvent |
|---|---|---|---|---|---|
| isopropyl | direct | —(CH₂)₄— | H | hydrogen oxalate 128–130 | acetonitrile |
| methyl | direct | —(CH₂)₆— | H | hydrogen oxalate 111–113 | acetonitrile |
| phenyl | —CH₂— | —CHCH₂—<br>\|<br>CH₃ | 2-cyano | 124–128 | ethyl acetate |

-continued

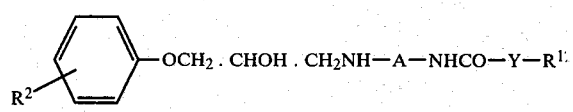

| R¹ | Y | A | R² | m.p.(°C.) | Crystallisation solvent |
|---|---|---|---|---|---|
| isopropyl | direct | $-\underset{\underset{CH_3}{\mid}}{C}HCH_2-$ | H | 124–126 | ethyl acetate |
| n-pentyl | direct | $-\underset{\underset{CH_3}{\mid}}{C}HCH_2-$ | H | 102–103 | ethyl acetate |
| isopropyl | direct | $-(CH_2)_3-$ | H | 94–95 | ethyl acetate |
| n-pentyl | direct | $-(CH_2)_6-$ | H | 85–86 | ethyl acetate |
| phenyl | $-CH_2-$ | $-\underset{\underset{CH_3}{\mid}}{C}HCH_2-$ | 2-nitro | 115–117 | ethyl acetate |
| phenyl | $-CH_2-$ | $-\underset{\underset{CH_3}{\mid}}{C}HCH_2-$ | 2-allyl-oxy | 102–105 | ethyl acetate |
| phenyl | $-CH_2-$ | $-\underset{\underset{CH_3}{\mid}}{C}HCH_2-$ | 3-methyl | hydrogen fumarate 87–90 | acetonitrile |
| phenyl | $-CH_2-$ | $-\underset{\underset{CH_3}{\mid}}{C}HCH_2$ | 3-bromo | 118–119 | ethyl acetate |
| 2-chloro-phenyl | $-CH_2-$ | $-\underset{\underset{CH_3}{\mid}}{C}HCH_2$ | 2-nitro | 98–101 | toluene |
| phenyl | $-CH_2-$ | $-\underset{\underset{CH_3}{\mid}}{C}HCH_2-$ | 3-methoxy | hydrogen fumarate 85–90 | ethyl acetate |
| phenyl | $-CH_2-$ | $-C(CH_3)_2CH_2-$ | 2-methyl | hemi-fumarate 189–190 | Aqueous Ethanol |
| phenyl 165 | $-CH_2-$ | $-C(CH_3)_2CH_2-$ | (1-naphthyl) | Hemi-Fumarate 194–195 | Aqueous ethanol |
| phenyl | $-CH_2-$ | $-\underset{\underset{CH_3}{\mid}}{C}HCH_2-$ | (1-naphthyl) | 127–128 | ethyl acetate |
| phenyl | $-CH_2-$ | $-C(CH_3)_2CH_2-$ | 2-cyano | hemi-fumarate 180–181 | aqueous ethanol |
| phenyl | $-CH_2-$ | $-C(CH_3)_2CH_2-$ | 2-chloro | hemi-fumarate 187–188 | aqueous ethanol |

EXAMPLE 5

A mixture of 2.5 g. of 1-p-benzyloxyphenoxy-2,3-epoxypropane, 1.16 g. of β-propionamidoethylamine and 20 ml. of isopropanol is heated under reflux for 3 hours and then cooled and evaporated to dryness under reduced pressure. The residue is suspended in acetic acid and shaken for 30 minutes in the presence of a 30% palladium-on-charcoal catalyst and in an atmosphere of hydrogen, at laboratory temperature and atmospheric pressure, when 255 ml. of hydrogen have been absorbed. The mixture is filtered, the filtrate is evaporated to dryness under reduced pressure and the residue is dissolved in methanol. A solution of oxalic acid in ether is added and the mixture is filtered. The solid residue is crystallised from a mixture of ethanol and ether and there is thus obtained 1-p-hydroxyphenoxy-3-β-propionamidoethylamino-2-propanol hemioxalate, m.p. 149° C.

The process described above is repeated except that the appropriate 1-benzyloxyphenoxy-2,3-epoxypropane (prepared by conventional means from the corresponding benzyloxyphenol and epichlorohydrin) and the appropriate β-substituted-ethylamine derivative are used as starting materials and there are thus obtained the compounds described in the following tables:

HO—C₆H₄—OCH₂.CHOH.CH₂NHCH₂CH₂NHCO—Y—R¹

| position of HO— substituent | R¹—Y— | base or salt | m.p.(°C.) | crystallis-ation solvent |
|---|---|---|---|---|
| 4- | methoxy-CH₂— | oxalate | 199 (with de- | ethanol |

| | | | | composition) | |
|---|---|---|---|---|---|
| 4- | phenyl- | | acetate | 145-146 | ethanol |
| 4- | phenyl-CH$_2$— | | hemi-oxalate hydrate | 110 (with decomposition) | ethanol |
| 3- | isopropyl | | base | (oil) | — |
| 2- | isopropyl | | hydrogen oxalate | 168-170 | ethanol/Acetonitrile |

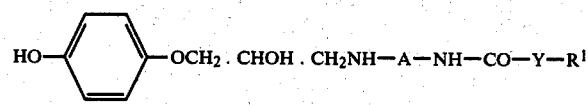

HO—⟨phenyl⟩—OCH$_2$ . CHOH . CH$_2$NH—A—NH—CO—Y—R$^1$

| R$^1$ | —Y— | A | m.p.(°C.) | Crystallisation solvent |
|---|---|---|---|---|
| isopropyl | direct | —CH$_2$CH$_2$— | hemioxalate quarter-hydrate 213 | ethanol |
| isopropyl | direct | CH$_3$<br>\|<br>—CH—CH$_2$— | hemioxalate quarter-hydrate 220 (with decomposition) | water |
| ethyl | —O— | —CH$_2$CH$_2$— | hemioxalate 189 | aqueous ethanol |
| n-heptyl | direct | —CH$_2$CH$_2$— | hemioxalate hydrate 95 | isopropanol |
| isopropyl | direct | —(CH$_2$)$_3$— | hemioxalate hemihydrate 179-180 | methanol/ether |

EXAMPLE 6

A mixture of 5.72 g. of 1-(3-hydroxymethyl-4-benzyloxyphenoxy)-2,3-epoxypropane, 4.40 g. of N-benzyl-N-β-isobutyramidoethylamine and 50 ml. of isopropanol is heated under reflux for 17 hours, cooled and evaporated to dryness under reduced pressure. The residue is dissolved in acetic acid and shaken for 19 hours in the presence of a 30% palladium-on-charcoal catalyst and in an atmosphere of hydrogen at laboratory temperature and atmospheric pressure, when 830 ml. of hydrogen have been absorbed. The mixture is filtered, the filtrate is evaporated to dryness and the residue is dissolved in ethanol. A solution of oxalic acid in ether is added, the mixture is filtered and the solid residue is crystallised from ethanol. There is thus obtained 1-(3-hydroxymethyl-4-hydroxyphenoxy-3-β-(isobutyramido)ethylamino-2-propanol hemioxalate hemi-hydrate, m.p. 148°-149° C.

The process described above is repeated except that 1-(3,4-dibenzyloxyphenoxy)-2,3-epoxypropane is used in place of 1-(3-hydroxymethyl-4-benzyloxyphenoxy)-2,3-epoxypropane. There is thus obtained 1-(3,4-dihydroxyphenoxy)-3-β-(isobutyramido)ethylamino-2-propanol hemioxalate, m.p. 168° C. with decomposition.

The various acylaminoalkylamine derivatives used as starting materials in Examples 1 to 6 may be obtained as described in U.S. Pat. No. 4,010,189.

EXAMPLE 7

A mixture of 0.64 g. of 3-benzylamino-1-phenoxy-2-propanol, 1.44 g. of β-(2-methyl-2-p-chlorophenoxybutyramido)ethyl chloride and 0.42 g. of sodium bicarbonate is heated at 120° C. for 18 hours and then cooled and stirred with 25 ml. of ethyl acetate and 25 ml. of water. The ethyl acetate phase is separated, dried over anhydrous magnesium sulphate and evaporated to dryness under reduced pressure. There is thus obtained as an oil, which is used without further purification, 1-phenoxy-3-[N-benzyl-N-β-(2-methyl-2-p-chlorophenoxybutyramido) ethyl]amino-2-propanol.

A mixture of 1.9 g. of the above compound, 40 ml. of ethanol, 1 ml. of 11 N-aqueous hydrochloric acid and 0.2 g of a 30% palladium-on-charcoal catalyst is shaken with hydrogen at laboratory temperature and atmospheric pressure until the uptake of hydrogen ceases. The mixture is filtered and the filtrate is evaporated to dryness under reduced pressure. The residue is dissolved in 50 ml. of ether and the solution is added to a solution of 0.6 g. of oxalic acid in 25 ml. of ethyl acetate. The mixture is filtered and the solid residue is crystallised from acetonitrile. There is thus obtained 1-phenoxy-3-β-(2-methyl-2-phenoxybutyramido)ethylamino-2-propanol oxalate, m.p. 112°-113° C.

EXAMPLE 8

A solution of 2.5 g. of 1-phenoxy-3-β-(p-benzyloxybenzamido)ethylamino-2-propanol (Example 1) in 50 ml. of a 1:1 v/v mixture of ethanol and acetic acid is shaken for 1 hour with hydrogen at laboratory temperature and atmospheric pressure in the presence of 400 mg. of a 5% palladium-on-charcoal, when 180 ml. of hydrogen have been absorbed. The mixture is filtered, the filtrate is evaporated to dryness under reduced pressure and the residue is dissolved in water. The solution is extracted with ethyl acetate and the extract is dried and evaporated to dryness. The residue is dissolved in ethyl acetate and a solution of oxalic acid in acetone is added. The mixture is filtered and the solid residue is crystallised from ethanol. There is thus obtained 1-phenoxy-3-β-(p-hydroxybenzamido)ethylamino-2-propanol hydrogen oxalate, m.p. 152°-154° C. (with decomposition).

The process described above is repeated except that 1-phenoxy-3-β-(2,5-dibenzyloxybenzamido)-ethylamino-2-propanol (oxalate m.p. 176°-178° C.; prepared as described in Example 1 from β-(2,5-dibenzyloxybenzamido)ethylamine, m.p. 96°-98° C.) or 1-phenoxy-3-β-(3,4-dibenzyloxybenzamido)ethylamino- 2-propanol (Example 1) is used as starting material. There are thus obtained respectively 1-phenoxy-3-β-(2,5-dihydroxybenzamido)ethylamino-2-propanol (hemioxalate m.p. 195°–197° C. after crystallisation from a mixture of ethanol and water), and 1-phenoxy-3-β-(3,4-dihydroxybenzamido)ethylamino-2-propanol, m.p. 178°–180° C. after crystallisation from ethanol.

EXAMPLE 9

A solution of 2.1 g. of trifluoroacetic anhydride in 5 ml. of toluene is added during 15 minutes to an ice-cooled solution of 3.0 g. of 1-phenoxy-3-(N-benzyl-N-β-aminoethyl)-amino-2-propanol and 1.01 g. of triethylamine in 30 ml. of toluene and the mixture is stirred for a further 30 minutes and then washed four times with 20 ml. of water each time. The toluene phase is separated, dried over anhydrous magnesium sulphate and evaporated to dryness under reduced pressure. The residue is dissolved in 50 ml. of ethanol and the solution is shaken with hydrogen in the presence of 0.5 g. of a 30% palladium-on-charcoal catalyst at laboratory temperature and atmospheric pressure until 230 ml. of hydrogen have been absorbed. The mixture is filtered, the filtrate is evaporated to dryness and the residue is crystallised from a mixture of ethyl acetate and petroleum ether (b.p. 60°–80° C.). There is thus obtained 1-phenoxy-3-β-trifluoroacetamidoethylamino-2-propanol, m.p. 106°–108° C.

EXAMPLE 10

A solution of 3.74 of 1-phenoxy-3-(N-benzyl-N-β-aminoethyl)amino-2-propanol, 0.6 g. of methyl formate and 1.68 g. of sodium bicarbonate in 40 ml. of n-propanol is heated under reflux for 18 hours and then evaporated to dryness under reduced pressure. The residue is shaken with hydrogen by a similar process to that described in Example 9, and there is thus obtained 1-phenoxy-3-β-formamidoethylamino-2-propanol, m.p. 107°–109° C. after crystallisation from ethyl acetate.

EXAMPLE 11

A solution of 2.8 g. of racemic 1-phenoxy-3-β-isobutyramidoethylamino-2-propanol in 25 ml. of ethanol is added to a solution of 2.9 g. of (−)-2,3: 4,6-di-O-isopropylidene-2-keto-L-gulonic acid hydrate in 25 ml. of ethanol and the mixture is kept at 4° C. for 18 hours and then filtered. The solid residue is crystallised four times from 10 ml. of ethanol each time, and there is thus obtained (−)-1-phenoxy-3-β-isobutyramidoethylamino-2-propanol (−)-2,3:4, 6-di-O-isopropylidene-2-keto-L-gulonate, m.p. 170°–172° C.

The above salt is stirred with aqueous 2 N-sodium hydroxide solution (3 ml.) and the mixture is extracted twice with ethyl acetate (5 ml. each time). The combined extracts are dried through a molecular sieve and are added to a solution of 0.6 g. of oxalic acid in 10 ml. of ethyl acetate. The mixture is filtered and the solid residue is washed with ether. There is thus obtained (−)-1-phenoxy-3-β-isobutyramidoethylamino-2-propanol oxalate, m.p. 148°–150° C. (with decomposition), $\alpha_d^{25}$—12.0° (c, 7.6% in water).

EXAMPLE 12

A mixture of 1-(2-cyanophenoxy)-3-(β-aminoethylamino)-2-propanol (132 g.) and ethyl 4-hydroxyphenylacetate (100 g.) is heated at 90° C. for 23 hours, cooled and dissolved in ethanol (2.5 liters). A solution of oxalic acid (70.5 g.) in ethanol (500 ml.) is added and the mixture is heated under reflux and quickly cooled and filtered. The solid residue is washed with ethanol and then suspended in water (2 liters), and sufficient aqueous 11 N-hydrochloric acid is added to produce a clear solution. The solution is neutralised to pH 8.5 with aqueous 10 N-potassium hydroxide solution, and the mixture is extracted three times with n-butanol (800 ml. each time). The combined extracts are washed twice with saturated aqueous potassium bicarbonate solution (300 ml. each time) and twice with water (500 ml. each time), and then evaporated to dryness under reduced pressure. The residue is crystallised from acetonitrile (300 ml.) and there is thus obtained 1-(2-cyanophenoxy)-3-β-(4-hydroxyphenylacetamido)ethylamino-2-propanol, m.p. 118°–120° C.

The 1-(2-cyanophenoxy)-3-(β-aminoethylamino)-2-propanol used as starting material may be obtained as follows:

A solution of 1-(2-cyanophenoxy)-2,3-epoxypropane (93.3 g.) in tetrahydrofuran (700 ml.) is added dropwise during 5 hours to stirred ethylenediamine (600 g.) and the mixture is stirred for a further 16 hours and then evaporated to dryness under reduced pressure. The residue is twice dissolved in water (500 ml.) and then evaporated to dryness, and then twice dissolved in toluene (500 ml.) and then evaporated to dryness. There is thus obtained as residue 1-(2-cyanophenoxy)-3-(β-aminoethylamino)-2-propanol.

EXAMPLE 13

Tablets are prepared by a conventional wet granulation process containing the following ingredients:

| | | |
|---|---|---|
| 1-(2-cyanophenoxy)-3-β-(4-hydroxyphenyl-acetamido)ethylamino-2-propanol | 2.5 | mg. |
| lactose | 310 | mg. |
| maize starch | 105 | mg. |
| magnesium stearate | 4.25 | mg. |

The tablets are then film-coated with a conventional hydroxypropyl methylcellulose based coating mixture.

EXAMPLE 14

Film-coated tablets are prepared in a similar way to that described in Example 13 except that amounts of ingredients are as follows:

| | | |
|---|---|---|
| 1-(2-cyanophenoxy)-3-β-(4-hydroxyphenyl-acetamido)ethylamino-2-propanol | 25 | mg. |
| lactose | 300 | mg. |
| maize starch | 105 | mg. |
| magnesium stearate | 4.25 | mg. |

The 1-(2-cyanophenoxy)-3-β-(4-hydroxyphenylacetamido)ethylamino-2-propanol used as active ingredient in the tablets described in Example 13 or Example 14 may be replaced by any of the compounds described in Examples 1 to 11.

What I claim is:

1. A pharmaceutical composition comprising as active ingredient a therapeutically effective amount of at least one alkanolamine selected from compounds of the formula:

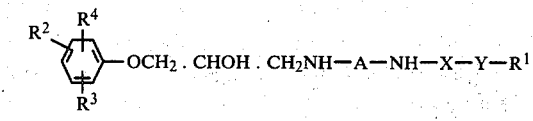

wherein A is alkylene of from 2 to 12 carbon atoms, wherein $R^1$ is hydrogen, or alkyl, halogenoalkyl, alkenyl or cycloalkyl each of up to 10 carbon atoms, or aryl of the formula:

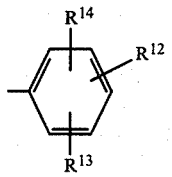

wherein $R^2$, $R^3$, $R^{12}$ and $R^{13}$, which may be the same or different, each is hydrogen, halogen, hydroxy, amino, nitro or cyano, alkyl, cycloalkyl, alkenyl, alkynyl, alkoxy, alkylthio, cycloalkoxy, alkenyloxy, alkynyloxy or alkanoyl each of up to 6 carbon atoms, or aryl, aryloxy or aralkoxy each of up to 12 carbon atoms; or wherein $R^2$ and $R^3$ together, and/or $R^{12}$ and $R^{13}$ together, are trimethylene, tetramethylene, 1-oxotetramethylene, propenylene, but-2-enylene or buta-1,3-dienylene such that together with the adjacent benzene ring they form respectively indanyl, 5,6,7,8-tetrahydronaphthyl, 5-oxo-5,6,7,8-tetrahydronaphthyl, indenyl, 5,8-dihydronaphthyl or naphthyl; wherein $R^4$ is hydrogen, hydroxy or hydroxymethyl or aralkoxy of up to 12 carbon atoms; wherein $R^{14}$ is hydrogen, amino or dialkylamino of up to 12 carbon atoms; wherein X is carbonyl (—CO—) and wherein Y is a direct link, or alkylene, oxyalkylene or alkyleneoxy each of up to 6 carbon atoms, or except when $R^1$ is hydrogen, oxygen; and the acid-addition salts thereof, in association with a pharmaceutically-acceptable diluent or carrier therefor.

2. A composition as claimed in claim 1 wherein A is ethylene, 1-methylethylene or 1,1-dimethylethylene, $R^1$ is hydrogen, or alkyl, alkenyl or cycloalkyl each of up to 6 carbon atoms, or trifluoromethyl, monohydroxyphenyl or dihydroxyphenyl, Y is a direct link, X is carbonyl, $R^2$ is hydrogen or chloro, cyano, nitro, methyl, allyl, methoxy or allyloxy in the ortho-position of the benzene ring and $R^3$ and $R^4$ are both hydrogen; or the acid-addition salts thereof.

3. A composition as claimed in claim 1 wherein A is ethylene, 1-methylethylene or 1,1-dimethylethylene, $R^1$ is phenyl, $R^{12}$ is hydrogen, chloro, nitro, hydroxy, methyl or methoxy, $R^{13}$ and $R^{14}$ are both hydrogen, Y is methylene, ethylene or methyleneoxy, X is carbonyl, $R^2$ is hydrogen or chloro, cyano, nitro, methyl, allyl, methoxy or allyloxy in the ortho- or meta- position of the benzene ring and $R^3$ and $R^4$ are both hydrogen; or the acid-addition salts thereof 4. A composition as claimed in claim 1 wherein A is ethylene, 1-methylethylene or 1,1-dimethylethylene, $R^1$ is hydrogen or alkyl of up to 6 carbon atoms, Y is methyleneoxy, X is carbonyl, and $R^2$ is hydrogen or chloro, cyano, nitro, methyl, allyl, methoxy or allyloxy in the ortho-position of the benzene ring and $R^3$ and $R^4$ are both hydrogen; or the acid-addition salts thereof.

5. A composition as claimed in claim 1 wherein A is ethylene, 1-methylethylene or 1,1-dimethylethylene, $R^1$ is alkyl or cycloalkyl each of up to 6 carbon atoms or phenyl, $R^{12}$ is hydrogen, methyl, methoxy or phenyl, $R^{13}$ and $R^{14}$ are both hydrogen, Y is a direct link or methylene, X is carbonyl, $R^2$ is hydrogen or hydroxy, $R^3$ is hydrogen and $R^4$ is hydroxy; and the acid-addition salts thereof.

6. A composition as claimed in claim 1 wherein A is ethylene, 1-methylethylene or 1,1-dimethylethylene, $R^1$ is alkyl of up to 6 carbon atoms, Y is oxygen or methyleneoxy, X is carbonyl, and $R^2$ is hydrogen or hydroxy, $R^3$ is hydrogen and $R^4$ is hydroxy or the acid-addition salts thereof.

7. A composition as claimed in claim 1 wherein the active ingredient is selected from the group consisting of 1-phenoxy-3-β-benzamidoethylamino-2-propanol;
1-phenoxy-3-β-phenylacetamidoethylamino-2-propanol;
1-phenoxy-3-β-phenoxyacetamidoethylamino-2-propanol;
1-phenoxy-3-(α-methyl-β-phenylacetamidoethyl)amino-2-propanol;
1-phenoxy-3-β-pivalamidoethylamino-2-propanol;
1-phenoxy-3-(β-isobutyramido-α-methylethyl) amino-2-propanol;
1-(2-nitrophenoxy)-3-β-isobutyramidoethylamino-2-propanol;
1-phenoxy-3-β-propionamidoethylamino-2-propanol;
1-phenoxy-3-β-hydroxyacetamidoethylamino-2-propanol;
1-(2-cyanophenoxy)-3-β-propionamidoethylamino-2-propanol;
1-phenoxy-3-β-(2-chlorophenylacetamidoethyl)amino-2-propanol;
1-phenoxy-3-β-butyramidoethylamino-2-propanol;
1-phenoxy-3-β-isobutyramidoethylamino-2-propanol;
1-phenoxy-3-β-(4-methoxyphenylacetamidoethyl)amino-2-propanol;
1-phenoxy-3-β-acetamidoethylamino-2-propanol;
1-(2-methoxyphenoxy)-3-β-isobutyramidoethylamino-2-propanol;
1-phenoxy-3-(α,α-dimethyl-β-isobutyramidoethyl) amino-2-propanol;
1-phenoxy-3-(α,α-dimethyl-β-phenylacetamidoethyl) amino-2-propanol; and the acid-addition salts thereof.

8. A composition as claimed in claim 1 wherein the active ingredient is selected from the group consisting of 1-(3,4-dihydroxyphenoxy)-3-β-isobutyramidoethylamino-2-propanol and the acid-addition salts thereof.

9. A composition as claimed in claim 1 wherein the active ingredient is selected from the group consisting of 1-(2-cyanophenoxy)-3-β-(4-hydroxyphenylacetamido) ethylamino-2-propanol and the acid-addition salt thereof.

10. A composition as claimed in claim 1 wherein the acid-addition salt is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-naphthoate), or a salt derived from a sulphonated polystyrene resin.

11. The compound 1-(2-cyanophenoxy)-3-β-(4-hydroxyphenylacetamido)ethylamino-2-propanol or an acid-addition salt thereof.

12. A method for the treatment or prophylaxis of heart diseases and hypertension in warm-blooded animals which comprises administering to said animals a therapeutically effective amount of at least one alkanolamine or salt thereof defined in claim 1.

13. A method for producing coronary β-adrenergic blockade in warm-blooded animals in need of such blockade which comprises administering to said animals a therapeutically effective amount of at least one alkanolamine or salt thereof defined in claim 1.

14. A method for the treatment of acute or chronic heart failure in warm-blooded animals which comprises administering to said animals a therapeutically effective amount of at least one cardiac stimulant alkanolamine or salt thereof defined in claim 1 wherein one or more of the substituents $R^2$, $R^3$ and $R^4$ is hydroxy.

* * * * *

UNITED STATES PATENT AND TRADEMARK OFFICE
CERTIFICATE OF CORRECTION

PATENT NO. : 4,167,581
DATED : September 11, 1979
INVENTOR(S) : Leslie H. Smith

It is certified that error appears in the above-identified patent and that said Letters Patent are hereby corrected as shown below:

In the Heading of the patent, under Item [30] add:

--Sept. 17, 1973 [GB] United Kingdom......43478/73--

Column 3, last line, change formula to read:

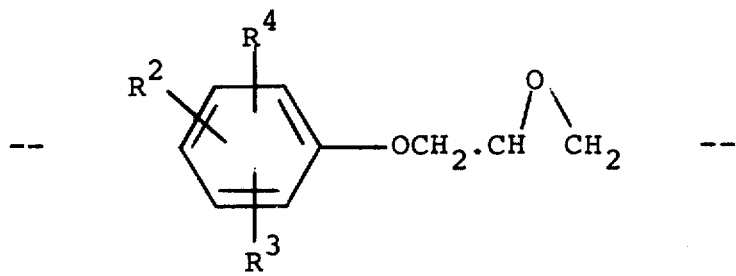

Signed and Sealed this

Eighth Day of July 1980

[SEAL]

Attest:

SIDNEY A. DIAMOND

Attesting Officer

Commissioner of Patents and Trademarks